United States Patent [19]

Weiss

[11] Patent Number: 5,018,044
[45] Date of Patent: May 21, 1991

[54] DUAL CONDUCTOR WRISTBAND

[75] Inventor: John W. Weiss, Austin, Tex.

[73] Assignee: Minnesota Mining and Manufacturing Company, St. Paul, Minn.

[21] Appl. No.: 397,997

[22] Filed: Aug. 23, 1989

[51] Int. Cl.$^5$ .......................... H05F 3/02; H01R 4/66
[52] U.S. Cl. .................................. 361/220; 361/212;
439/37; 439/92; 439/669
[58] Field of Search .................... 439/669, 909, 37, 92;
361/220, 212, 219, 223, 224; 174/5 R, 5 SB;
57/901; 128/381, 382, 384–389, 796

[56] References Cited

U.S. PATENT DOCUMENTS

| | | | |
|---|---|---|---|
| 3,015,754 | 1/1962 | Legge | 317/2 |
| 3,857,397 | 12/1974 | Brosseau | 128/384 |
| 4,373,175 | 2/1983 | Mykkanen | 361/220 |
| 4,398,277 | 8/1983 | Christiansen et al. | 361/220 |
| 4,402,560 | 9/1983 | Swainbank | 339/11 |
| 4,459,633 | 7/1984 | Vandermark | 361/220 |
| 4,475,141 | 10/1984 | Antonevich | 361/220 |
| 4,525,014 | 6/1985 | Holman et al. | 439/92 |
| 4,537,462 | 8/1985 | Manabe | 339/259 |
| 4,577,256 | 3/1986 | Breidegam | 361/220 |
| 4,583,797 | 4/1986 | Engelmore et al. | 339/6 R |
| 4,605,984 | 8/1986 | Fieldler | 361/220 |
| 4,619,275 | 10/1986 | Ross et al. | 361/220 |
| 4,638,399 | 1/1987 | Maroney et al. | 361/220 |
| 4,639,825 | 1/1987 | Breidegam | 361/212 |
| 4,662,695 | 5/1987 | Gordon et al. | 339/14 R |
| 4,680,668 | 7/1987 | Belkin | 361/220 |
| 4,695,116 | 9/1987 | Bailey et al. | 439/188 |
| 4,698,724 | 10/1987 | Burvee | 361/220 |
| 4,720,764 | 1/1988 | Lucas | 361/212 |
| 4,720,765 | 1/1988 | Weiss | 361/220 |
| 4,745,519 | 5/1988 | Breidegam | 361/220 |
| 4,755,144 | 7/1988 | Gordon et al. | 439/37 |
| 4,782,425 | 11/1988 | Breidegam | 361/212 |
| 4,802,056 | 1/1989 | Aronson | 361/212 |
| 4,816,964 | 3/1989 | Weiss | 361/220 |
| 4,845,585 | 7/1989 | Weiss | 361/220 |

FOREIGN PATENT DOCUMENTS

2547390  5/1977  Fed. Rep. of Germany.

OTHER PUBLICATIONS

EOS/ESD Standard No. 1 published by EOS/ESD Association, Inc. in Jan. 1987.
EIA Standard RS–453 published by Electronic Industries Association in May 1978.

*Primary Examiner*—Todd E. DeBoer
*Assistant Examiner*—Richard T. Elms
*Attorney, Agent, or Firm*—Gary L. Griswold; Walter N. Kirn; Jack V. Musgrove

[57] ABSTRACT

A dual conductor wristband utilizing a two-wire tether having a modified phono-type plug. The wristband includes a strap and a connector case, the case having a female jack for receiving the dual connector plug. The plug diameter is smaller than conventional plugs, and the diameter of the pilot hole for the plug tip is correspondingly smaller to prevent accidental connection to a non-grounding tether. Two alternative embodiments are presented for coupling the dual connector plug to two electrically isolated backplates on the connector case. Each backplate is connected to one of the two conductive pathways on the strap.

19 Claims, 2 Drawing Sheets

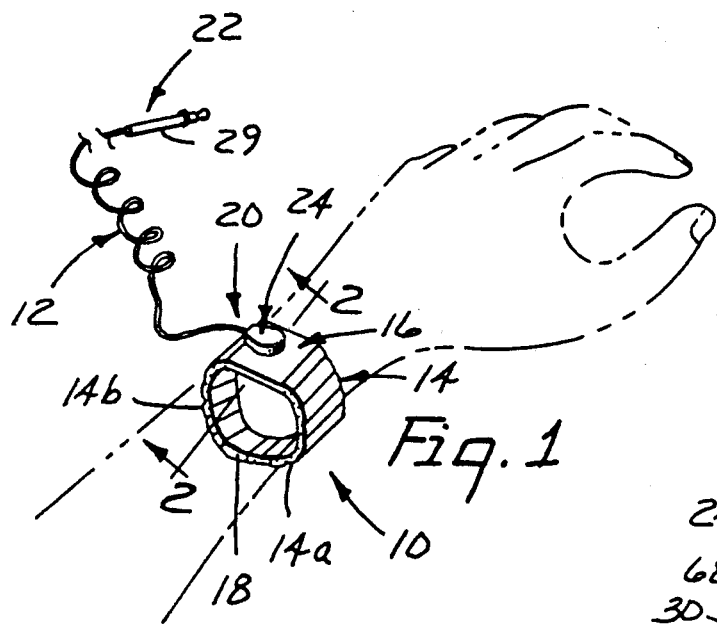
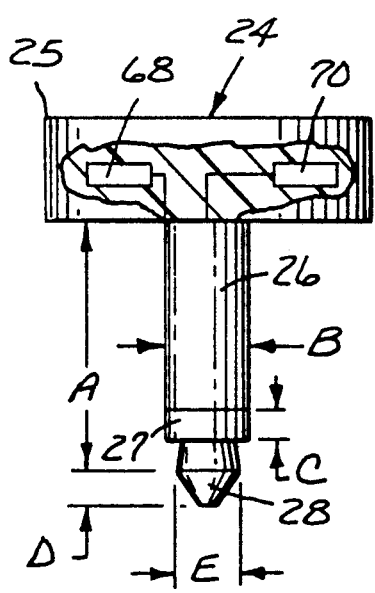
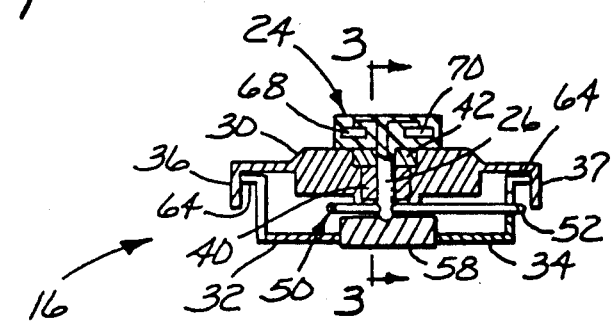
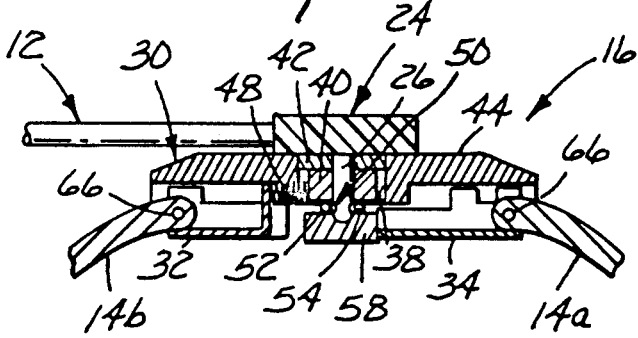
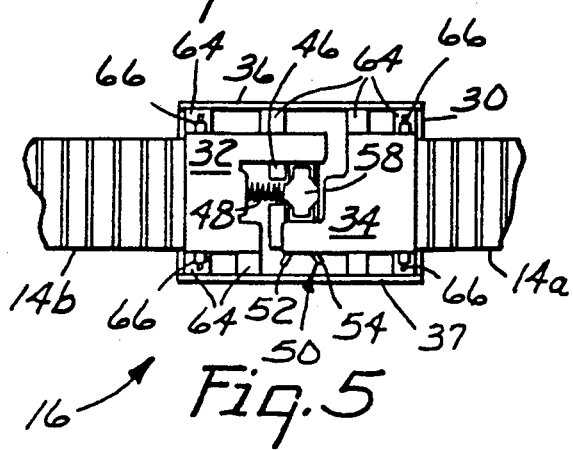
Fig. 1
Fig. 2
Fig. 3
Fig. 5
Fig. 6

DUAL CONDUCTOR WRISTBAND

BACKGROUND OF THE INVENTION

1. Field of the Invention

The present invention generally relates to devices for preventing electrostatic discharge, and more particularly to a wristband having two separate conductive paths therein, the wristband and conductive paths being connected to a conductive grounding tether having two wires.

2. Description of the Prior Art

Electrostatic discharge, as well as the mere presence of a static electric field, can be extremely detrimental to sensitive electronic parts. This is particularly true of modern semiconductors and integrated circuits which may be degraded or destroyed by the buildup of static electricity in the workplace. Especially sensitive components can be severely affected by an electrical potential as small as 50 volts, yet the simple act of walking has been known to triboelectrically generate a potential of 30,000 volts or more.

The most common tool heretofore used in the battle against electrostatic discharge is a conductive tether which is designed to drain away excess electrostatic charge. One of the earliest grounding tethers is described in U.S. Pat. No. 3,015,754 issued to W. Legge, which illustrates a grounding strap for a human leg, with a tether connecting the strap to a conductive tread to be attached to the bottom of a shoe. Later devices incorporated a wrist strap, and several variations of the wrist strap and/or grounding tether are disclosed in numerous patents.

The subject invention relates to a wrist strap having two separate conductive pathways and, accordingly, the closest prior art is probably U.S. Pat. No. 4,639,825. Such a dual conductor wristband is useful in conjunction with systems which monitor the resistance of the grounding tether, for example, the system shown in FIG. 11 of Breidegam. In order to interface a dual conductor wristband with such a monitor, however, a two-wire tether is also necessary. In fact, the subject invention deals not so much with the wristband itself, but rather with the connection means between the dual conductor wristband and the two-wire tether.

Examples of two-wire tethers appear in several patents, viz., U.S. Pat. Nos. 4,605,984 (Fiedler), 4,638,399 (Maroney et al.), 4,639,825 (Breidegam), and 4,720,764 (Lucas). Unfortunately, each of the two-wire tethers disclosed in these patents suffers from serious drawbacks. For example, the tether disclosed in Fiedler is shorted at the distal end which is totally unacceptable for use with the type of monitor described in Breidegam. Maroney et al. depicts the use of a shielded cable whose conductors are similarly shunted at the distal end and hence likewise worthless for use with the present invention. The tether of Breidegam is essentially two separate tethers joined along the length of the wires with two snap connectors at the proximate end for connection to the wristband. The provision of two separate connectors, however, creates a problem for the wearer in that movements of the wrist, arm and hand may cause the two lines emanating from the snap connectors to become tangled up, possibly even causing one connector to become disconnected. Conversely, rotational interference between the two connectors may inhibit the dexterity of the wearer, which affects performance on the assembly line. Finally, the wires in the Lucas tether are shorted together at both ends, which is clearly unacceptable. It would, therefore, be desirable and advantageous to devise means for connecting a two-wire tether to a dual conductor wristband which would overcome the above-noted problems.

Accordingly, the primary object of the present invention is to provide a dual conductor wristband for drainage of excess electrostatic charge.

Another object of the invention is to provide such a wristband having a single female jack for connection to a two-wire grounding tether.

Still another object of the invention is to provide a two-wire grounding tether which cooperates with the movements of the individual wearing the wristband.

Yet another object of the invention is to provide a wristband which prevents accidental connection to a source of electrical potential.

SUMMARY OF THE INVENTION

The foregoing objects are achieved in a dual conductor wristband having a connector case including a female jack for receiving a dual-connector phono-type plug. The phono plug is attached to the terminal end of a two-wire grounding tether, and preferably has non-standard dimensions to prevent accidental use of a tether which is not designed for grounding purposes. The case further includes means for electrically isolating the two conductive portions of the wristband from one another, and for connecting each of the conductive portions to one of the wires in the two-wire tether via the modified phono plug. Alternative embodiments are provided for both metal wristwatch type bands and fabric bands.

BRIEF DESCRIPTION OF THE DRAWINGS

The novel features of the invention are set forth in the appended claims. The invention itself, however, will best be understood by reference to the accompanying drawing wherein:

FIG. 1 is a perspective view showing the dual conductor wristband and attached grounding tether with the user's hand in dashed lines.

FIG. 2 is a cross-sectional view of the connector case of the dual conductor wristband taken along lines 2—2 of FIG. 1.

FIG. 3 is a cross-sectional view of the connector case of the dual conductor wristband taken along lines 3—3 of FIG. 2.

FIG. 5 is a bottom plan view of the case and dual conductor wristband.

FIG. 6 is a front elevational view of the phono plug utilized by the present invention, illustrating its non-standard dimensions.

DESCRIPTION OF THE PREFERRED EMBODIMENT

Figure 4:
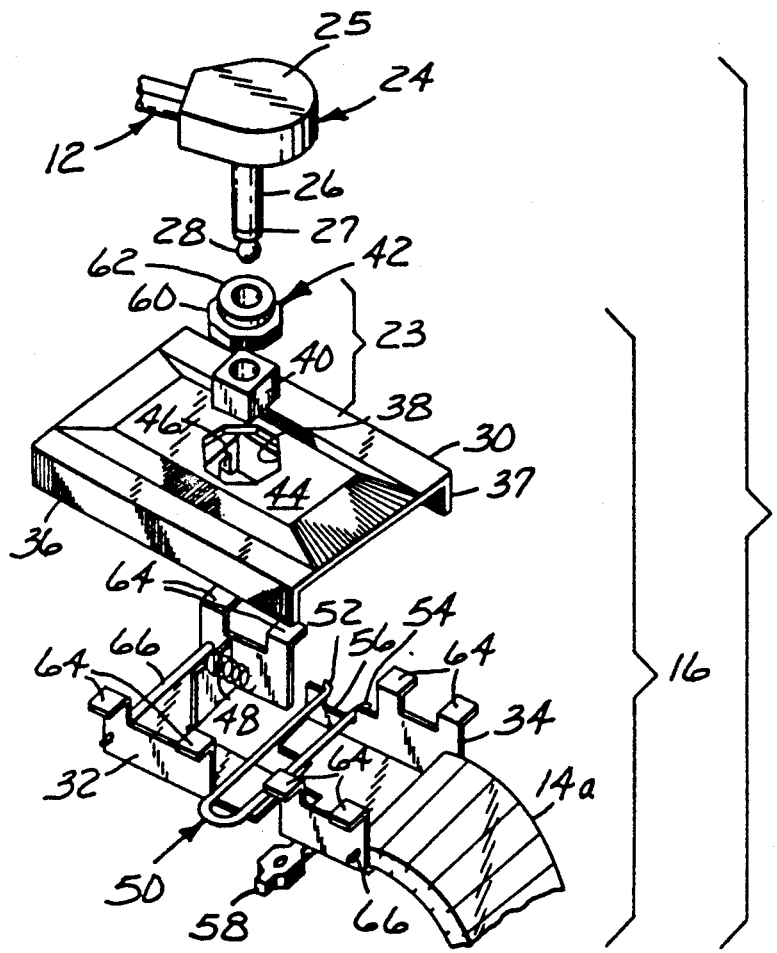
FIG. 4 is an exploded perspective view showing the connector case structure.

With reference now to the figures, and in particular with reference to FIG. 1, there is depicted a dual conductor wristband 10 and a grounding tether 12 positioned on a hand shown in dashed lines. Dual conductor wristband 10 is generally comprised of a strap 14 and a connector module or case 16. In the embodiment shown, strap 14 is constructed of a plurality of metallic links, forming two strap sections 14a and 14b, separated by an electrically insulative buckle 18. Strap sections 14a and 14b are thereby electrically isolated from one another, forming two separate conductive paths in strap 14. Strap 14 may either be of fixed circumference, or expandable as shown in U.S. Pat. No. 4,459,633 issued to H. Vandermark on July 10, 1984. Further details of the construction of strap 14 (as well as the fabric strap shown in FIG. 7) may be found in U.S. Pat. No. 4,638,825 issued to A. Breidegam on Jan. 27, 1987. General standards for grounding wristbands may also be found in EOS/ESD STANDARD NO. 1, published by the EOS/ESD Association, Inc., of Westmoreland, N.Y. (January 1987).

Tether 12 is comprised of two insulated wires, and has a proximate end 20 and a distal end 22. A modified dual connector phono plug 24 is attached to proximate end 20 of tether 12 for connection to a female jack 23 in connector case 16. Phono plug 24 has a head 25, and a sleeve 26 and tip 28, separated by a small insulator band 27. In the preferred embodiment, a second phono plug 29 is attached to distal end 22 of tether 12. During use of wristband 10, phono plug 29 is connected to an external monitor (not shown); such monitors are conventionally known and may check the integrity of the wristband in addition to insuring a proper connection to ground. Other details of tether 12 are discussed below in conjunction with FIG. 6.

Referring now to FIGS. 2 through 5, various features of connector case 16 of dual conductor wristband 10 are explained. Case 16 is comprised of a cover 30, and two contact plates which may conveniently be referred to as sleeve backplate 32 and tip backplate 34 (alluding to the sleeve and tip portions of phono plug 24). Cover 30 is generally rectangular in shape, and has two side rails 36 and 37 running parallel to strap 14. Cover 30 may be constructed of any non-conductive material, preferably one which may be injection molded and ultrasonically welded, such as nylon or polypropylene.

Cover 30 also has a void 38 therein for receiving a barrel contact 42 and pilot washer 42. Void 38 has a generally cubic shape, corresponding to the shape and size of barrel contact 40, and is open at the upper surface 44 of cover 32. One of the side walls defining void 38 further has an aperture 46 therein to allow passage of a coil spring 48 which abuts barrel contact 40. Coil spring 48 is mounted on a tine (obscured in the drawings by spring 48) which emanates from and is integral with sleeve backplate 32. As can best be seen in FIG. 3, void 38 is actually wider than barrel contact 40, and spring 48 thereby serves to bias barrel contact 40 to a position slightly offset from the centerline defined by pilot washer 42. This creates a camming action as phono plug 24 is inserted into case 16, and insures reliable electrical connections between phono plug sleeve 26, barrel contact 40, coil spring 48, and sleeve backplate 32. Barrel contact 42 is preferably constructed of nickel plated brass.

After phono plug 24 passes through barrel contact 40, tip 28 snaps into a hairpin contact 5o. Hairpin contact 50 has two ends 52 and 54, and is attached to tip backplate 34 by clipping ends 52 and 54 into a slot 56 in backplate 34. The distance between the legs of hairpin contact 50 is slightly smaller than the diameter of tip 28; this means that, as tip 28 snaps into place, the legs will spread slightly. This in turn increases the contact force between ends 52 and 54 and slot 56, optimizing electrical conductivity to tip backplate 34. This movement also provides a wiping action against hairpin contact 50 which cleans the contact surfaces thereof. Hairpin contact 50 may be constructed of any metallic substance, such as stainless steel. In the preferred embodiment, the contact position of tip 28 is stabilized by a (concave) pilot hole in a seat 58 below hairpin contact 50. Seat 58 is formed integrally with cover 22.

Assembly of connector Case 16 may best be understood with reference to FIG. 4. Barrel contact 40 and pilot washer 42 (which, together with hairpin contact 50 and seat 58, form female jack 23 in the preferred embodiment) are first lowered into void 38 in cover 30. Pilot washer 42 includes a flanged portion 60 and a hub portion 62. After placement of both of the elements in void 38 cover 30 is ultrasonically welded in the area proximate thereto, resulting in a buildup of plastic material about flange 60. This secures washer 42 and barrel contact 42 in void 38. Hub 62 serves to guide plug 24 into (offset biased) barrel contact 40.

The next step is to attach spring 48 to the tine extending from sleeve backplate 32, and position hairpin contact 50 just above seat 58 of cover 32. Each of the backplate may then be affixed to cover 30. As sleeve backplate 32 is moved adjacent to cover 30, spring 48 is threaded through aperture 46 and brought in contact with barrel contact 40. As tip backplate 34 is moved adjacent to cover 30, the ends 52 and 54 of hairpin contact 50 are inserted into slot 56 of backplate 34. Each of the backplates is then secured to cover 30 by ultrasonic welding; plastic from cover 30 near rails 36 and 37 flows and then stiffens around a plurality of outwardly projecting tabs 64 formed integrally with the backplates. For clarity, the figures show tabs 64 before welding.

Strap sections 14a and 14b may be attached to backplates 32 and 34 before or after assembly of connector case 22. Strap 14 may advantageously be made replaceable by the provision of pins 66 as used in conventional watch bands. Alternatively, the leading edge of the backplates may be formed into a flange (not shown) which would attach to strap 14 between its metallic links. After the two strap sections 14a and 14b have been attached to the backplates, they may be joined together by means of insulative buckle 18. Backplates must obviously be made of a conductive material, preferably stainless steel.

With reference now to FIG. 6, details of tether 12 and phono plug 24 are explained. FIG. 6 is a front elevational view of plug 24, illustrating various dimensions thereof by use of reference letters A through E. In the preferred embodiment, these dimensions are as follows:

| Reference Letter | Dimension | Preferred Value | Range (mm) |
| --- | --- | --- | --- |
| A | barrel length | 7.37 mm (0.29 in) | 7.0–7.6 |
| B | barrel diam. | 3.51 mm (0.138 in) | 3.4–3.6 |
| C | insulator ht. | 0.89 mm (0.035 in) | 0.6–1.2 |
| D | tip length | 1.27 mm (0.05 in) | 1.0–1.5 |
| E | tip diameter | 2.92 mm (0.115 in) | 2.8–3.1 |

These dimensions are smaller than the standard dimensions prescribed for dual connector phono plugs. In other words, phono plug 24 is both shorter and of smaller diameter than conventional phono plugs. Standard dimensional characteristics for phono plugs may be found in EIA STANDARD RS-453 published by the Electronic Industries Association (May 1978).

The inner diameter of the pilot hole in seat 58 is accordingly just slightly larger than the tip diameter of plug 24, but not large enough to accept a standard plug (i.e., not greater than about 3.2 millimeters). This is highly desirable for use with a grounding wristband, in order to insure that only a proper grounding tether has been connected to the wristband. In laboratory workstations where these devices are used, there are commonly several different electrical systems at work, some utilizing phono-type plugs. By providing a non-standard plug (and smaller pilot hole for the plug tip), damage to the wearer resulting from accidental connection to a high-voltage source is avoided. The diameter of pilot washer 42 may optionally also be smaller than the diameter of standard phono-plug barrels. The dimensions of plug 24 may be even smaller than the ranges specified above, but it is anticipated that the ranges given will be optimal. Down sizing of the plug is also desirable for maintaining a low-profile connection with case 16.

Another important feature of tether 12 is the manner in which the tether itself is connected to plug 24. For ease of use, tether 12 preferably emerges from plug 24 at a right angle to sleeve 26, i.e., sleeve 26 is essentially normal to head 25. When combined with a male axial connector, this allows plug 24 to swivel a full 360° without becoming tangled or inhibiting the dexterity of the user, unlike prior art dual conductor wristband tethers. The provision of a normal plug also lessens the likelihood of unintended removal of plug 24 from connector case 26. Torsional or rotational forces will not cause plug 24 to become disconnected; rather, it must be pulled straight out, unlike the snap connectors used in the prior art.

Plug 24 contains two current limiting resistors 68 and 70 which are electrically connected to sleeve 26 and tip 28, respectively. The provision of such resistors minimizes the chances of accidental shock arising from current surges in the ground line or unintentional connection of tether 12 to a high-voltage source. The preferred resistance of resistors 68 and 70 is one megohm, although the value could vary within the range of 500 kΩ to 5 MΩ (no resistors are necessary in a well protected environment). As those skilled in the art will appreciate, the effective resistance of these two resistors, when acting in parallel, is half of either of them, i.e., using two 1 MΩ resistors results in an effective resistance of 500 kΩ. The values of the resistances are primarily a safety consideration and may further be affected by future EOS/ESD standards.

Current limiting resistors 68 and 70 are preferably located at the proximate end 22 of tether 12 to optimize their effectiveness. If either of the wires in tether 12 were to become exposed to a high-voltage source between ends 22 and 22, the resistors would be ineffective if placed at the distal end 22 thereof. In this regard it should be noted that distal plug 29 is of conventional dimensions, which precludes connection of plug 29 to female jack 23; this assures the user that resistors 68 and 70 are located proximate to wristband 10. In the preferred embodiment, distal plug 29 is aligned with the wires, unlike the 90° orientation of plug 24.

Figure 7:
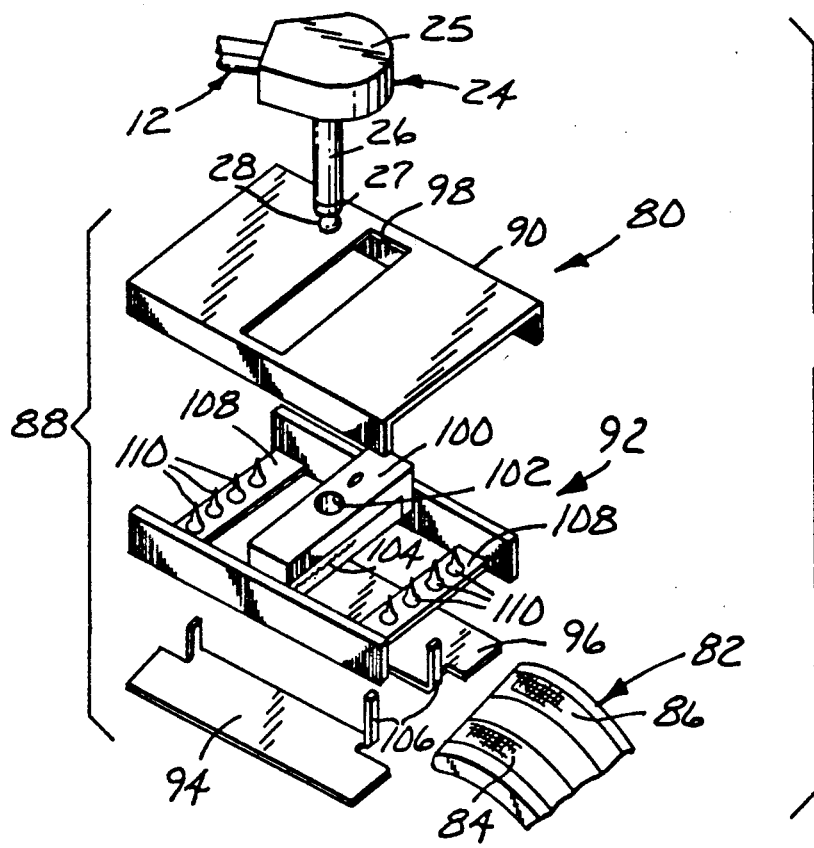
FIG. 7 is an exploded perspective view showing an alternative embodiment of the dual conductor wristband of the present invention for a fabric-type band.

Referring now to FIG. 7, an alternative embodiment 80 of the dual conductor wristband of the present invention is shown. As disclosed in U.S. Pat. No. 4,639,825 (mentioned above), the strap portion of a dual conductor wristband may be constructed of either metallic links or of a fabric band. Alternative dual conductor wristband 80 is designed for use with a fabric band 82 having two parallel conductive strips 84 and 86 therein. Alternative connector case 88 now includes a cover 90, an intermediate buckle 92, and backplates 94 and 96.

Cover 90 is similar to cover 30, but void 38 has been replaced by a slot 98. Slot 98 receives a connector block 100 integral with buckle 92. Connector block 100 has a hole (with an inner diameter of 3.6 mm or less) therein for receiving plug 24, with two wires 102 and 104 located along the surface of the hole for connection to sleeve 26 and tip 28 of plug 24, respectively. When alternative dual conductor wristband is assembled, a portion of wire 102 is in contact with backplate 96 and a portion of wire 104 is in contact with backplate 94. Backplates 94 and 96 may be attached to buckle 92 by securing tabs 106 to ribs 108 of buckle 92. Tabs 106 may also pierce fabric band 82 and thereby secure it to connector case 88. Alternatively, ribs 108 may be provided with a plurality of spikes 110 as taught by U.S. Pat. No. 4,720,765 (Weiss) in order to secure fabric band 82, and/or a clasp with a living hinge (not shown) may be provided as taught by U.S. Pat. No. 4,845,585 (Weiss).

Although the invention has been described with reference to specific embodiments, this description is not meant to be construed in a limiting sense. Various modifications of the disclosed embodiment, as well as alternative embodiments of the invention, will become apparent to persons skilled in the art upon reference to the description of the invention. It is therefore contemplated that the appended claims will cover such modifications that fall within the true scope of the invention.

I claim:

1. A connector case for a wristband having two conductive paths, comprising:
    electrically insulative cover means having a void therein;
    female jack means attached to said cover means for receiving a dual connector plug, said female jack means including a barrel contact located within said void of said cover means, said barrel contact having a hole therethrough for passage of a dual connector plug, and a hairpin contact located proximate said barrel contact for receiving a tip of a dual connector plug;
    a first conductive backplate attached to said cover means and in electrical contact with said barrel contact;
    a second conductive backplate attached to said cover means and in electrical contact with said hairpin contact; and
    means for attaching said first and second conductive backplates to the two conductive paths of the wristband.

2. The connector case of claim 1 wherein said female jack means prevents entry of a plug having a tip diameter of greater than about 3.1 millimeters.

3. The connector case of claim 1 further comprising:
    a pilot washer attached to said cover means adjacent said barrel contact, said pilot washer defining a centerline; and
    bias means for positioning said barrel contact offset from said centerline when no plug is present therein.

4. The connector case of claim 3 wherein said cover means further includes a seat member adjacent said hairpin contact having a pilot hole therein for receiving the tip of the dual connector plug, said pilot hole having an inner diameter of no greater than about 3.2 millimeters.

5. A dual conductor wristband for draining electrostatic charge, comprising:
 a strap member having first and second conductive pathways, said pathways being electrically isolated from each other;
 a first conductive backplate attached to said strap member and in electrical contact with said first conductive pathway thereof;
 a second conductive backplate attached to said strap member and in electrical contact with said second conductive pathway thereof;
 an electrically insulative cover attached to said first and second backplates, said cover having a void therein; and
 a female jack located proximate said first and second backplates for receiving a dual connector plug, said female jack including:
  a barrel contact located within said void, said barrel contact having a hole therethrough for passage of a dual connector plug and being electrically connected to said first backplate, and
  a hairpin contact located proximate said barrel contact for receiving a tip of the dual connector plug, said hairpin contact being electrically connected to said second backplate.

6. The dual conductor wristband of claim 5 wherein said female jack further has a seat member adjacent said hairpin contact, said seat member having a pilot hole therein for receiving a tip of the dual connector plug, said pilot hole having an inner diameter of no greater than about 3.2 millimeters.

7. The dual conductor wristband of claim 5 further comprising:
 a pilot washer attached to said cover adjacent said barrel contact, said pilot washer defining a centerline; and
 bias means for positioning said barrel contact offset from said centerline when no plug is present therein.

8. The dual conductor wristband of claim 7 wherein said cover further includes a seat member adjacent said hairpin contact having a pilot hole therein for receiving the tip of the dual connector plug, said pilot hole having an inner diameter of no greater than about 3.2 millimeters.

9. A tether for a dual conductor wristband having two separate conductive pathways, comprising:
 first and second insulated wires each having distal and proximate ends;
 means for electrically connecting said distal ends of said first and second wires to an external monitor; and
 a dual connector plug having sleeve and tip portions, attached to said proximate end of said wires, said first wire being electrically connected to said sleeve portion of said dual connector plug, and said second wire being electrically connected to said tip portion of said dual connector plug, said tip portion further having a diameter of no greater than about 3.1 millimeters.

10. The tether of claim 9 wherein said dual connector plug has a head portion, and said wires emerge from said head portion essentially perpendicular to said sleeve and tip portions.

11. The tether of claim 10 further comprising first and second resistors, said first resistor being electrically connected in series with said first wire, and said second resistor being electrically connected in series with said second wire.

12. The tether of claim 11 wherein said first and second resistors are both located in said head portion of said dual connector plug.

13. An apparatus for draining electrostatic charge from an individual, comprising:
 a tether including:
  first and second insulated wires each having distal and proximate ends,
  means for electrically connecting said distal ends of said first and second wires to an external monitor, and
  a dual connector plug having a sleeve and a tip, attached to said proximate end of said wires, said first wire being electrically connected to said sleeve of said dual connector plug, and said second wire being electrically connected to said tip of said dual connector plug;
 a connector case including:
  an insulative cover,
  a female jack attached to said cover for receiving said dual connector plug, said female jack having first and second contacts for connection with said sleeve and tip, respectively, of said dual connector plug,
  a first conductive backplate attached to said cover and electrically connected to said first contact of said female jack,
  a second conductive backplate attached to said cover and electrically connected to said second contact of said female jack; and
 a strap attached to said connector case, having first and second conductive pathways electrically isolated from each other, said first conductive pathway being electrically connected to said first backplate and said second conductive pathway being electrically to said second backplate.

14. The apparatus of claim 13 wherein said tip of said dual connector plug has a diameter of no greater than about 3.1 millimeters, and said cover further includes a seat adjacent said second contact having a pilot hole therein for receiving said tip of said dual connector plug, said pilot hole having an inner diameter of no than about 3.2 millimeters.

15. The apparatus of claim 13 wherein said dual connector plug has a head, said wires emerging from said head essentially perpendicular to said sleeve and tip, and further comprising first and second resistors, said first resistor being electrically connected in series between said first wire and said sleeve of said dual connector plug, and said second resistor being electrically connected in series between said second wire and said tip of said dual connector plug, said first and second resistors both being located in said head of said dual connector plug.

16. The apparatus of claim 13 wherein:
 said cover has a slot therein; and
 said connector case further includes a buckle located between said cover and said backplates, said buckle having a connector block engaging said slot, said connector block having a hole therein, said hole defining said female jack.

17. The apparatus of claim 13 wherein:
 said cover has a void therein;

said first contact comprises a barrel contact located within said void, said barrel contact having a hole therethrough for receiving said sleeve of said dual connector plug, and being electrically connected to said first backplate; and said second contact comprises a hairpin contact located proximate said barrel contact for receiving said tip of said dual connector plug, said hairpin contact being electrically connected to said second backplate.

18. The apparatus of claim 17 further comprising:

a pilot washer attached to said cover adjacent said barrel contact, said pilot washer defining a centerline; and bias means for positioning said barrel contact offset from said centerline when no plug is present therein.

19. A case for connecting a wristband having two conductive paths to a phono-type dual connector plug having sleeve and tip portions, the case comprising:

female jack means for receiving the dual connector plug, said female jack means including first means for contacting the sleeve portion of the dual connector plug, said first contacting means having an effective diameter, and second means for contacting the tip portion of the dual connector plug, said second contacting means including seat means having an effective diameter which is less than said effective diameter of said first contacting means;

a first conductive backplate attached to said female jack means and in electrical contact with said first contacting means;

a second conductive backplate attached to said female jack means and in electrical contact with said second contacting means; and means for attaching said first and second conductive backplates to the two conductive paths of the wristband.

* * * * *